United States Patent
Schusser et al.

(10) Patent No.: US 8,848,863 B2
(45) Date of Patent: Sep. 30, 2014

(54) NON-PARALLEL GRATING ARRANGEMENT WITH ON-THE-FLY PHASE STEPPING, X-RAY SYSTEM

(75) Inventors: Sebastian Schusser, Aachen (DE); Gereon Vogtmeier, Aachen (DE)

(73) Assignee: Koninklijke Philips N.V., Eindhoven (NL)

( * ) Notice: Subject to any disclaimer, the term of this patent is extended or adjusted under 35 U.S.C. 154(b) by 159 days.

(21) Appl. No.: 13/514,061

(22) PCT Filed: Dec. 3, 2010

(86) PCT No.: PCT/IB2010/055562
§ 371 (c)(1),
(2), (4) Date: Jun. 6, 2012

(87) PCT Pub. No.: WO2011/070489
PCT Pub. Date: Jun. 16, 2011

(65) Prior Publication Data
US 2012/0236985 A1    Sep. 20, 2012

(30) Foreign Application Priority Data
Dec. 10, 2009   (EP) .................................... 09178705

(51) Int. Cl.
*A61B 6/00* (2006.01)
*G21K 1/06* (2006.01)

(52) U.S. Cl.
CPC . *G21K 1/06* (2013.01); *A61B 6/484* (2013.01); *G21K 2201/06* (2013.01); *G21K 2207/005* (2013.01)
USPC ............................................. 378/16; 378/62

(58) Field of Classification Search
CPC ..... G21K 1/06; G21K 2207/005; A61B 6/484
USPC .............................. 378/16, 19, 36, 37, 62, 145
See application file for complete search history.

(56) References Cited

U.S. PATENT DOCUMENTS
2011/0243305 A1*  10/2011  Tada .............................. 378/87

FOREIGN PATENT DOCUMENTS
EP         1731099         12/2006
WO      WO2009115966      9/2009

* cited by examiner

*Primary Examiner* — Courtney Thomas (57) ABSTRACT

The present invention relates to X-ray image acquisition technology in general. Employing phase-contrast imaging for X-ray image acquisition may significantly enhance the visibility of structures in images acquired. However, phase-contrast information may only be obtainable in a small detector region with subsequent image acquisitions requiring individual phase stepping states to allow reconstruction of an X-ray image. Accordingly, a grating arrangement for phase-contrast imaging is provided which may allow on the fly phase stepping during a field of view scan. According to the present invention a grating arrangement (1) for phase-contrast imaging is provided, comprising a first grating element (8) and a second grating element (10). Each of the first grating element (8) and the second grating element (10) comprises a trench structure. The trench structure comprises at least one trench region (9) and at least one barrier region (3). The at least one trench region (9) and the at least one barrier region (3) are at least locally arranged in parallel. The first grating element (8) and the second grating element (10) are arranged such that the trench structure of the first grating element (8) and the trench structure of the second grating element (10) are non-parallel comprising an angle α.

21 Claims, 4 Drawing Sheets

NON-PARALLEL GRATING ARRANGEMENT WITH ON-THE-FLY PHASE STEPPING, X-RAY SYSTEM

FIELD OF THE INVENTION

The present invention relates to X-ray image acquisition in general. More particularly, the present invention relates to image acquisition employing phase-contrast. In particular, the present invention relates to a grating arrangement for phase-contrast imaging, an X-ray system and to the use of a grating arrangement in at least one of an X-rays system, a transmission X-ray system, a CT system and a tomosynthesis system.

BACKGROUND OF THE INVENTION

In X-ray image acquisition technology, an object to be examined, e.g. a patient, is situated between an X-ray generating device or X-ray source, e.g. an X-ray tube, and an X-ray detector. A fan-beam or cone-beam is generated by the X-ray source, possibly employing collimation elements, in the direction of the X-ray detector. The object to be examined situated in the path of the X-radiation is spatially attenuating the X-ray beam, depending on its inner structure. The spatially attenuated X-radiation is subsequently arriving at the X-ray detector, with the intensity distribution of the X-radiation being determined and subsequently converted to electrical signals for further processing and display of an X-ray image.

Both the X-ray generating device and the X-ray detector may be mounted on a gantry for rotation about the object to be examined. By providing an according rotation with subsequent acquisition of different X-ray images of varying alignment and orientation with respect to the object to be examined, a three-dimensional reconstruction of the objects inner morphology may be obtained.

However, a certain object may have only a minor attenuation of X-radiation or differences in attenuation even within different tissues in the inside of the object, thus resulting in a rather uniformly attenuated X-ray image having low contrast and so impeding distinguishing individual elements of the interior of the object to be examined. While different regions within the object may have similar attenuation properties, they may influence a phase of X-radiation penetrating the object to a larger extent.

Thus, phase-contrast imaging may be employed for visualization of phase information of X-radiation, in particular, at least partly, coherent X-rays, passing an object to be examined. In addition to X-ray transmission imaging taking into account only amplitude attenuation of X-radiation, phase-contrast imaging may not only determine absorption properties of an object to be examined along a projection line, but also the phase-shift of transmitted X-rays. A detected phase-shift may thus provide additional information that may be employed for contrast enhancement, determining a material composition, possibly resulting in a reduction in X-radiation dosage.

Since a phase of a wave may not be measured directly, a conversion of a phase-shift into an intensity modulation by interference of two or more waves may be employed.

In differential phase contrast imaging, the use of a cone-beam geometry may constitute a limitation of the usable size of an X-ray detector element, in particular when the phase and/or the absorption gratings are aligned with their trenches parallel to the optical axis. At a distance of about 1m from the x-ray source, the point where the phase-sensitivity drops significantly with respect to the central region of the imaging system is about +−3 cm off the optical axis. This limitation may in particular depend on grating properties, visibility, distance and angle of a cone beam or fan beam.

For some applications, e.g. medical imaging applications, inspection imaging applications or security imaging applications, a field of view of fewer than 6 cm, at least in one direction of a two-dimensional X-ray image may be too small to be feasibly reasonable. Moreover, for phase contrast imaging, multiple images of a region have to be acquired, having individual phase stepping states for a preferred reconstruction of image information.

Thus, there may be a desire to increase the field of view of an image obtainable when employing phase-contrast imaging while reducing acquisition steps necessary due to phase stepping while acquiring image information.

SUMMARY OF THE INVENTION

Thus, a grating arrangement is provided, which allows for a scanning of a desired field of view while providing on the fly phase stepping.

According to an exemplary embodiment of the present invention, a grating arrangement for phase-contrast imaging is provided, comprising a first grating element and a second grating element. Each of the first grating element and the second grating element comprises a trench structure, wherein the trench structure comprises at least one trench region and at least one barrier region. The at least one trench region and the at least one barrier region are at least locally arranged in parallel and wherein the first grating element and the second grating element are arranged such that the trench structure of the first grating element and the trench structure of the second grating element are non-parallel comprising an angle α.

According to a further exemplary embodiment of the present invention, an X-ray system is provided, comprising an X-ray source and a grating arrangement according to the present invention, further comprising an X-ray detector element. An object is arrangeable between the X-ray source and the grating arrangement and the X-ray source and the grating arrangement are operatively coupled such that a phase-contrast image of the object is obtainable.

According to a further exemplary embodiment of the present invention, a grating arrangement according to the present invention is used in at least one of an X-ray system, a CT system and a tomosynthesis system.

For obtaining phase information of an X-ray beam an interferometer may be employed. Preferably coherent X-radiation passes through an object to be examined subsequently arriving at an X-ray detector. Since phase information may not be measured directly, the implications of a constructive or destructive interaction of two or more wave fronts, possibly resulting in an intensity modulation detectable by an X-ray detector, may be employed.

An according interference may be obtained by providing a phase-shifting grating or a beam splitter grating between the object to be examined and the X-ray detector. X-radiation passing the beam splitter grating thus results in an interference pattern behind the beam splitter grating, containing information about a phase-shift within the X-ray beam in the relative positions of its minima and maxima, i.e. the respective local intensity of the X-ray beam. The resulting intensity pattern comprises minima and maxima having a distance typically in the order of several micrometers.

However, an X-ray detector may only comprise a resolution in the order of ~50 to 150 μm and may thus not be able to resolve an accordingly fine structure of the generated interference pattern. Accordingly, a phase analyzer grating or absorber grating may be employed, comprising a periodic pattern of transmitting and absorbing strip elements or trench regions and barrier regions, having a periodicity similar to that of the interference pattern.

By illumination of the beam splitter grating alone, an interference pattern may be generated at the location of the analyzer grating, even in the absence of the latter. The analyzer grating may thus only be required due to x-ray detector elements employed, which do not provide a spatial resolution high enough to detect the interference pattern or fringes of the beam slitter grating directly. Because of this, the analyzer may be employed. In one phase-stepping position, it lets the fringe maxima pass through to the detector, after transverse displacement, the maxima may be absorbed in the gold trenches.

By the similar periodicity of the analyzer grating, an intensity modulation pattern may be generated behind the analyzer grating on the surface of the X-ray detector. An according pattern may have a substantially larger periodicity, which may thus be detectable by an X-ray detector having a resolution in the order of 50 to 150 μm. The X-ray detector element pixels may detect the interference pattern as averaged intensity values. To obtain a phase-contrast image, in particular for obtaining the differential phase-shift, the analyzer grating may be required to be shifted laterally, i.e. in a direction perpendicular to the grids or strips of both the analyzer grating and the beam splitter grating, which gratings are arranged substantially parallel with regard to the grating strips, by fractions of the grating pitch p, which may be in the order of 1 μm. E.g., the position from one grating gap or trench region to a subsequent grating gap may be changed in the order of e.g. 4 times or 8 times. An according lateral shift by fractions of the grating pitch p may be referred to as phase stepping. An X-ray beam passing through the grating in a single phase stepping instance thus comprises an individual phase stepping state.

The phase-shift may then be extracted from the intensity modulation observed in the X-ray detector element behind both grids during the phase stepping measured for each position, e.g. for each phase stepping state, of the analyzer grating. In particular, by measuring a plurality of positions, e.g. 4 or 8 positions having a different phase stepping state, phase information may be obtainable. Due to an incident angle of the X-rays onto the gratings, the visibility may be seen as decreasing for larger off axes positions with regard to a lateral extension to the trenches of the gratings. To assure sufficient visibility and thus detectability of the x-ray phase by the X-ray detector, a field of view may be limited to the size of about 6 cm, e.g. in case of system lengths, the distance between X-ray source and X-ray detector element, of about 1 m, energies of about 20-30 kVp and a trench structure having parallel structure. One solution to increase the field of view may be seen as moving an X-ray detector thus obtaining multiple sub-regions of a field of view subsequently. Since for each position of the X-ray detector an individual phase stepping, i.e. e.g. 4 or 8 individual image acquisitions having a different phase stepping state, may be required, an according movement, displacement, tilt or rotation of an X-ray detector combined with an according phase stepping may be a prolonged process.

In conventional absorption contrast projection imaging, a multitude of object structures along the direction of the incoming X-rays is superimposed in the transmission or projection image. This may often complicate determining individual structures and thus diminish the readability of an according X-ray image. An improvement in image quality may be obtained by distributing the total radiation dose over several angular views for improving depth information about the objects inner structure. An according technique may be referred to as tomosynthesis and may be employed in particular for acquiring three-dimensional volumetric image data. An according system may require the X-ray source and the X-ray detector being arranged on a gantry for rotation about the object to be examined. Also, the X-ray source may be shifted, in particular in a lateral movement, relative to the object to be examined and thus the detector Even in phase-contrast imaging a single projection may comprise superimposed structures and thus may also benefit from a tomosynthesis mode of operation. Accordingly, employing a phase-contrast system capable of tomosynthesis may overcome the diminished readability by superposition of anatomical structures.

The requirement of sufficient fringe visibility of, e.g. sufficiently large intensity modulations in phase-contrast imaging, in particular differential phase-contrast imaging, may impose restriction on the degrees of freedom of relative motion between an X-ray source and the gratings. In general, only a relative movement of the X-ray source along the grating trenches may be permitted. Thus, by providing a tomosynthesis movement in the direction parallel to the trenches of the silicon grids of the gratings compatibility between tomosynthesis and phase-contrast imaging may be achieved. Thus, it may be seen as being beneficial for the angle of incidence, measured within a plane perpendicular to the grating trenches, of X-radiation onto the gratings to not increase above a certain level during a tomosynthesis scan.

Extending the field of view by moving the X-ray detector thus scanning the X-ray detector through the field of view may require performing phase stepping for each position of the X-ray detector within the field of view. E.g., in a particular position a phase stepping of 4 or 8 image acquisition steps each having a different phase stepping state may be required. Subsequently, the X-ray detector may be displaced to acquire a sub-region of the field of view substantially adjacent to the previous arrangement within the field of view subsequently employing phase stepping with 4 or 8 image acquisition steps for acquiring phase-contrast image information of the second sub-region of the field of view. However, the X-ray detector may not be required to be displaced in the magnitude of the extension or width of the X-ray detector itself, but may rather be displaced only by a fraction, like ¼ or ⅛ of the extension of the X-ray detector or its active area for X-ray acquisition, possibly even only by one X-ray detector element pixel, with a concurrent phase stepping to acquire X-ray image information not only of a slightly different sub-region of the field of view, possibly overlapping with the previous sub-region by ¾ or ⅞ but also having a different phase stepping state required for the subsequent generation of X-ray image information employing phase-contrast. The pixel offset may allow the simultaneous detection of different phase stepping states, possibly in slightly different places. The displacement of ¼ or ⅛ may be interpreted as that a pixel would acquire such an offset with the same value as the measurement with a phase step of ¼ or ⅛, e.g. in case the object may be homogeneous in the area of the total pixel, comprising the sub-pixels. This may limit spatial resolution. The combination of a displacement by a certain pixel count and a reduced number of phase steps may be conceivable, e.g. either by a sequential scan with phase stepping or by acquiring all steps simultaneously with phase shifted sub-pixels or a combination thereof.

From a practical point of view, e.g. with regard to manufacturing an apparatus according to the present invention, the trenches of the gratings may preferably be perpendicular to the flat surface of the X-ray detector.

Conventionally, the beam-splitter grating and the analyzer grating may be manufactured from silicon wafers. For the analyzer grating, a further electro-plating process may be required, in order to fill the trenches with a highly absorbing material, e.g. gold. The manufacturing process may e.g. start with the application of a passivation layer followed by an etching procedure. The regions covered by the passivation layer may not be affected by the etching process, thus resulting in a trench pattern typically required. However, it may be difficult to etch trenches in a direction different from the direction perpendicular to the wafer surface. For a cone-beam x-ray phase-contrast system, the etch direction may depend strongly on the position on the wafer, such that the trenches may be focused to a predefined position designed to coincide later with the x-ray source position.

An according arrangement may be seen as being in particular responsible for reducing visibility of structures when departing from the optical axis in the range of about 6 cm. In particular, a distance of about 1 m between X-ray source and X-ray detector may limit the detector size to about 6 cm, e.g. in case of about 20-30 keV.

Phase-contrast imaging may be implemented beneficially when employing a, at least partly, coherent X-ray source. However, since a coherent X-ray source may in particular only be provided by e.g. a synchrotron, a further grating, a source grating may be employed between the X-ray source and the object in the beam path of the X-rays for generating a plurality of individual coherent X-ray sources, e.g. with grating elements which trenches are filled with absorbing material to build a plurality of µ-focus X-ray spots or lines next to each other. Alternatively, a plurality of individual, substantially coherent, X-ray sources, e.g. distributed X-ray sources, like carbon nanotube based emitters may be employed.

For obtaining subsequent phase-contrast images, in particular for being able to reconstruct a phase-contrast image or a differential phase-contrast image from acquired phase-contrast image information, a different phase stepping state for each phase-contrast image acquired with respect to a detector element pixel or at least a detector element row or detector element column is required. In other words, considering a fixed detector element, subsequent phase-contrast images require a change in phase stepping state to allow subsequent reconstruction of a phase-contrast image for multiple acquired image information. In case of a fixed detector, an according difference in phase stepping state, thus an individual phase stepping state may be acquired by displacing the beam splitter grating $G_1$ relative to the analyzer grating $G_2$ by a fraction of the grating period p.

In case of a moving X-ray detector element, an according phase stepping, thus change in phase stepping state may be achievable on the fly in accordance with the present invention.

According to the present invention, an individual phase stepping state of each X-ray detector element pixel, pixel row or pixel column may be obtainable by tilting the trench structure of one of the grating elements relative to the trench structure of the other grating by a small angle α. The angle α may in particular depend on parameters like size of an X-ray detector element pixel, the grating pitch and number of required/desired phase stepping states. E.g. with a grating element pitch displacement of 2 µm over 8 pixel rows, e.g. for 8 different, individual phase stepping states, α max be approximately 0.1°, for an assumed pixel size of 150 µm. In case of a smaller pixel size, the value of the angle may increase.

Having an according grating arrangement with one trench structure tilted or rotated relative to the other trench structure phase stepping may be considered to be provided by moving the unit of detector elements and grating elements, thus the grating arrangement, lateral to detector rows, which may occur during a scanning of the field of view. In other words, e.g. when displacing the X-ray detector and the grating arrangement as a single unit by the size of one X-ray detector element pixel, e.g. by a single row or column, depending on the direction of movement, the respective arrangement of beam splitter grating $G_1$ and analyzer grating $G_2$ comprises a different relative alignment towards one another when seen from the X-ray source in the direction of the X-ray detector, in particular for a single pixel, row or column. Furthermore, a grating element having a trench structure with a lateral discrete trench shift, e.g. for each pixel row, may be implemented. An according discrete lateral trench shift may thus represent an individual phase stepping state.

E.g., in case a certain structure of the object to be examined is detectable by an X-ray detector element column having a defined arrangement of beam splitter grating $G_1$ and analyzer grating $G_2$, a shift or displacement in a scanning movement may result in the same structure being detectable by a further X-ray detector element row having, due to the displacement, differently aligned gratings $G_1$ and $G_2$ relative to one another, due to the tilt or angulation of the grating structure of the two gratings. An according shift of displacement may in particular be a linear shift or a rotatory displacement. However, further arbitrary displacements may be conceivable, which may provide an alignment position of the two grating elements having differing phase stepping states, e.g. 4 or 8 different phase stepping states.

Thus, when the grating arrangement comprising an X-ray detector having a size smaller than the field of view, is scanned or moved through the field of view for acquiring a larger X-ray image, the phase stepping state may be seen as being changed on the fly with the scanning movement. An individual, thus completely unique phase stepping state of a single X-ray detector element pixel, row or column may not be required. E.g., in case 4, 8 or 9 individual phase-contrast images are acquired for subsequent calculating an X-ray image, 4, 8 or 9 individual, distinct unique phase stepping states may be sufficient. However, in this case it may be required to displace the grating arrangement and the X-ray detector element such that a certain structure of the object to be examined is arranged relative to the grating arrangement and the X-ray detector such that a different phase stepping state is engaged.

E.g. in case exemplary 8 individual phase stepping states are provided, thus the grating arrangement having a period of 8 relative to individual X-ray detector element pixels, rows or columns, it should be avoided to displace the grating arrangement and the X-ray detector by a number of pixels equalling the period or a multiple of the period. E.g. in case of a period of 8 a scanning movement with displacing the grating arrangement and the X-ray detector element by 8 pixels should be avoided while displacing the same arrangement by 9 pixels, 11 pixels, 13 or 15 pixels etc. may be preferred. The detector may also be displaced by 1, 2, 3, 4, 5, 6 or 7 pixels.

Further, phase-contrast imaging may be performed by also employing two absorption gratings, instead of one phase and one absorption grating. A phase stepping in accordance with the present patent application may thus be required as well.

Also, it may be required to collimate X-radiation dynamically with regard to a moving X-ray detector element for assuring that only X-radiation detected is allowed to pass through the object.

The object may also be arranged between a first grating element and a second grating element, in particular between a beam splitter grating and an analyzer grating.

The scanning or displacement motion of the X-ray detector element through or over the field of view may not be required to be a pure lateral displacement however may also be circular movement, sinusoidal movement, zigzag movement or even an arbitrary movement, possibly controlled by a computer system. Also, a combined displacement of the above may be employed. In the following, further exemplary embodiments of the present invention are described relating in particular to a grating arrangement and to an X-ray system. However, it should be noted that the according explanations apply to all of the grating arrangement, the X-ray system and the use of a grating arrangement.

It should be noted that arbitrary variations and interchanges of single or multiple features between claims and in particular claimed entities are conceivable and within the scope and disclosure of the present patent application.

According to a further exemplary embodiment of the present invention, the first grating element and the second grating element may be arranged substantially parallel. According to a further exemplary embodiment of the present invention, the first grating element may be provided as a beam splitter grating and/or the second grating element may be provided as an analyzer grating.

An according arrangement comprising a beam splitter grating and an analyzer grating may allow for the acquisition of phase-contrast image information.

According to a further exemplary embodiment of the present invention, the grating arrangement may further comprise an X-ray detector element having a detector size, wherein the X-ray detector element may be arranged substantially perpendicular to at least one of the first grating element and the second grating element.

The inclusion of an X-ray detector element into the grating arrangement allows to provide a compact unit, possibly with defined relationships of the individual elements to one another for acquiring phase-contrast image information. The individual elements may be arranged substantially adjacent to one another or may be arranged having a defined distance, thus a gap between individual elements may be provided.

According to a further exemplary embodiment of the present invention, at least one of the first grating element and the second grating element is adapted to influence at least one parameter of an amplitude and a phase of electromagnetic radiation.

Thus, the grating elements are provided as an X-ray active element. According to a further exemplary embodiment of the present invention a may be in the range of approximately 1° to 0.01°, in particular 0.1°, 0.2° or 0.3°. According to a further exemplary embodiment of the present invention, the X-ray detector element may comprise an array of X-ray detector element pixels wherein at least one of an X-ray detector element pixel, an X-ray detector element pixel row and an X-ray detector element pixel column may comprise an individual phase stepping state.

In other words, the arrangement of the first grating element and the second grating element atop X-ray detector element, when seen from the direction of the X-ray source and the object to be examined respectively, is provided with an individual phase stepping state in particular individual, unique phase stepping states for each of the X-ray detector element pixel, the X-ray detector element pixel row and X-ray detector pixel column. However, a unique phase stepping state may not be required, rather a dedicated minimal number of different phase stepping states may be sufficient, e.g. 4 or 8. An according number of image acquisition steps may be seen as sampling if intensity values of a "quasi-sinus-shaped" curve. 4 different phase stepping states may be sufficient, with more individual steps providing better signal quality, however may require an increased time interval for acquisition and may increase exposure dose. Depending on the geometry of the grating elements employed, a plurality of different phase stepping states may be acquired simultaneously.

E.g. acquisition of different phase stepping states may be performed simultaneously, however at different locations. E.g. four adjacent sub pixels, constituting a pixel, may comprise four different phase stepping states. Thus, for the pixel, four different phase stepping states may be acquired, however with possibly reducing spatial resolution.

According to a further exemplary embodiment of the present invention, the X-ray system may be adapted for acquiring a phase-contrast image having a field of view larger than the detector size, wherein the grating arrangement may be displaceable and wherein, by the displacement of the grating arrangement, a phase-contrast image of the field of view may be obtainable.

Thus, by a movement of the grating arrangement in particular a scanning movement with an on the fly phase stepping, a phase-contrast image of a field of view larger than the detector size may be obtainable.

According to a further exemplary embodiment of the present invention, the X-ray detector element may be adapted for acquiring a sub-region of the field of view. Accordingly, the total field of view may be larger than the size of the X-ray detector element.

According to a further exemplary embodiment of the present invention, the X-ray detector and/or the grating arrangement may be adapted for scanning the field of view.

Thus, by a scanning movement a field of view is obtainable which may not be limited by the X-ray detector element size but rather by the implementation of the scanning movement.

According to a further exemplary embodiment of the present invention, the X-ray detector element and/or the grating arrangement may be displaceable from a first position and/or orientation for acquiring first contrast image information to a second position and/or orientation of acquiring second phase-contrast information.

Accordingly, by a displacement, which may be substantially the size of the X-ray detector element or a fraction thereof, e.g. ¼, ⅛ or ⅕, or even only one X-ray detector pixel, different phase-contrast information may be acquired, which may subsequently be employed for generating an X-ray image of the field of view.

According to a further exemplary embodiment of the present invention, the X-ray system may further comprise a third grating element, in particular a source grating or source grating element.

By providing a source grating between the X-ray source and the object to be examined in the path of the X-ray beam, a possibly incoherent X-ray source may be employed for phase-contrast imaging.

According to a further exemplary embodiment of the present invention, the X-ray source and/or the third grating element may be displaceable relative to at least one of the first grating element, the second grating element, the object and the X-ray detector element.

Here, a scanning movement may be implemented by a movement of the X-ray source and/or the third grating element relative to e.g. the object for providing different views or projections of X-radiation through the object arriving at the gratings and subsequently the X-ray detector.

These and other aspects of the present invention will become apparent from and elucidated with reference to the embodiments described hereinafter.

Exemplary embodiments of the present invention will be described below with reference to the following drawings.

The illustration in the drawings is schematic. In different drawings, similar or identical elements are provided with similar or identical reference numerals.

Figures are not drawn to scale, however may depict qualitative proportions.

DETAILED DESCRIPTION OF EMBODIMENTS

Figure 1A:
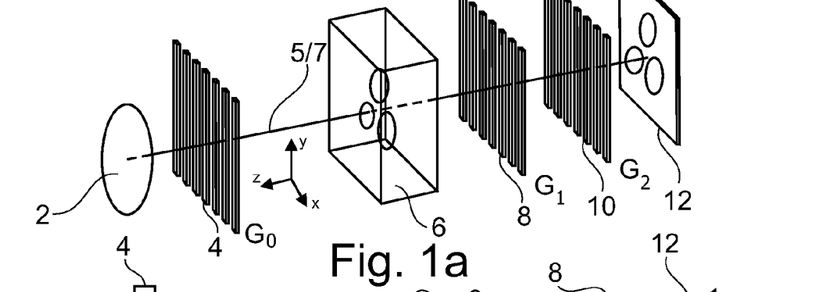
FIGS. 1a-c show an exemplary embodiment of an apparatus for phase-contrast imaging according to the present invention.
Figure 1B:
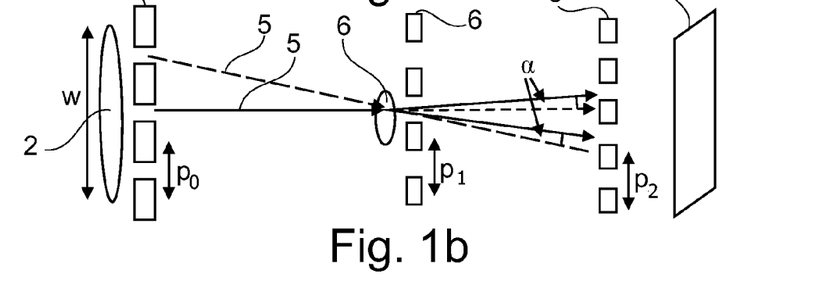
Figure 1C:
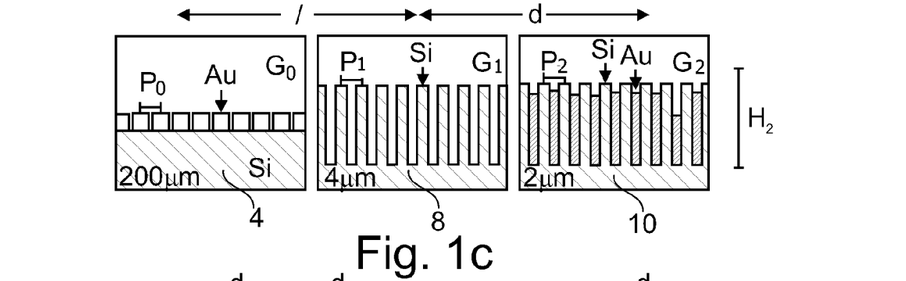

Now referring to FIGS. 1a-c, an exemplary embodiment of an apparatus for phase-contrast imaging according to the present invention is depicted.

FIG. 1a shows a three-dimensional representation of an exemplary embodiment of an apparatus for phase-contrast imaging. A rather large X-ray source 2 is arranged adjacent to a source grating 4. Since X-ray source 2 may be considered to be incoherent due to its size with respect to the wavelength of the radiation emitted, the source grating $G_0$ 4 is employed for providing a plurality of single coherent X-ray sources as depicted by the two arrows in FIG. 1b.

X-radiation 5 is emanating from X-ray source 2 in the direction of the optical axis 7 possibly constituting a fan-beam or cone-beam of X-rays. The respective shape of the X-ray beam is not depicted in FIG. 1a.

X-radiation 5 is arriving at object 6, penetrating object 6, subsequently arriving at a beam splitter grating $G_1$ 8. The trenches or gaps of the beam splitter grating 8 alter the phase of passing electromagnetic radiation with respect to the solid areas of the beam splitter grating, the barrier regions. Accordingly, a phase shift by $\phi$, in particular by $\pi$, is performed. An attenuation of X-radiation passing the barrier region compared to X-radiation passing the trench region may be neglectable. A source grating 4 may have a grating period of 50 to 200 µm, e.g. 57 µm, and may be made of a silicon substrate having a grating structure made e.g. from gold (Au). A beam splitter grating 8 may have a grating period of 4 µm and may be made of a silicon substrate having a grating structure made also from silicon, e.g. by an etching process for removing the material to constitute a trench structure. A analyser grating 10 may have a grating period of 2 µm and may be made of a silicon substrate having a grating structure made also from silicon, e.g. by an etching process for removing the material to constitute a trench structure, with the gaps or trenches filled with a high-z material, e.g. gold (Au).

An analyzer grating 10 $G_2$ is arranged between the beam splitter grating $G_1$ 8 and the X-ray detector 12. The distance between the source grating and the beam splitter grating 8 is depicted as 1 whereas the distance between the beam splitter grating 8 and the analyzer grating 10 is depicted as distance d. The multiple waves originating from the beam splitter grating 8 $G_1$ in the direction of the X-ray detector are arriving at the analyzer grating 10 $G_2$, subsequently producing an intensity modulation pattern (see FIG. 2) on the surface of the X-ray detector 12.

By shifting the beam splitter grating 8 versus the analyzer grating 10, thus displacing of gratings relative to one another, in particular with a fraction of the grating period $p_1$ or $p_2$, a plurality of intensity modulations induced by the phase stepping may be obtainable by the image detector 12, since the individual phase stepping states are different between individual phase steppings, i.e. alignment of $G_1$ versus $G_2$. Accordingly, by a plurality of Moiré patterns, an X-ray image of the object to be examined may be generated. Distance 1 may be of the order of 50-150 cm, e.g. 80 cm, however even a few meters may be conceivable, and distance d may be of the order of 2-20 cm, depending on the Talbot order chosen in the design of the interferometer, radiation energy and the grating pitch. The first fractional Talbot distance is in the order of 50 mm for 17 keV radiation energy or 120 mm for 25 keV radiation energy. Higher orders of the Talbot distance, e.g. n=3, 5, 7, are integer multiplies of these distances. Distance d of the first fractional Talbot distance may be calculated by equation 1 with M=magnification factor due to beam geometry, $p_1$=grating pitch of phase grating $G_1$ and $\lambda$=wavelength of the mean radiation energy used for phase contrast:

$$d = M \cdot \frac{p_1^2}{8 \cdot \lambda} \qquad \text{Equation 1}$$

Now referring to FIG. 1c, exemplary cross-sections of gratings $G_0$ to $G_2$ are depicted. Gratings $G_0$ and $G_2$ may in particular be filled with gold (Au). Gratings $G_1$ and $G_2$ may be implemented by etching a silicon based material for providing the trenches of the gratings. The grating period $p_0$ of the source grating may be in the order of 200 µm, even smaller, the grating period $p_1$ of $G_1$ may exemplary be in the range of 2 to 6 µm, in particular 4 µm and the grating period $p_2$ of $G_2$ may exemplary be in the range of 1 to 3 µm, in particular 2 µm.

Figure 2:
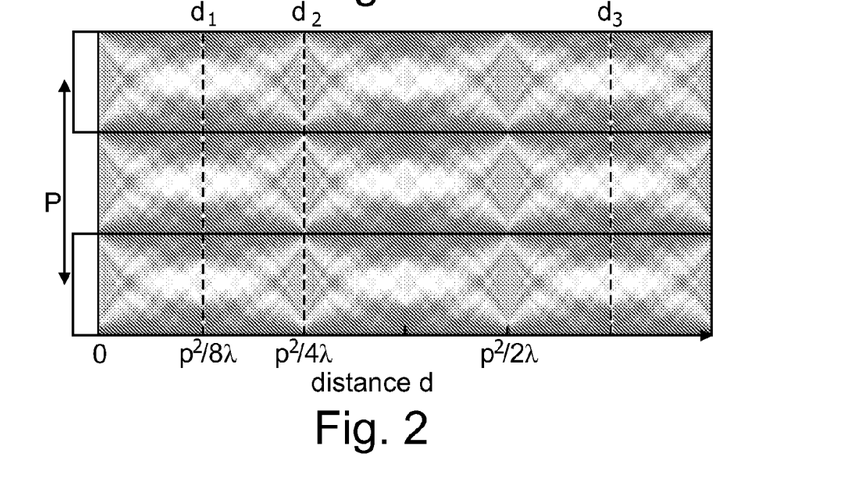
FIG. 2 shows an exemplary embodiment of an interference pattern according to the present invention, FIGS. 3a,b show exemplary phase-contrast images acquired according to the present invention.

Now referring to FIG. 2, an exemplary embodiment of an interference pattern according to the present invention is depicted.

FIG. 2 depicts an interference pattern created between beam splitter grating $G_1$ 8 and analyzer grating $G_2$ 10, demonstrating the self imaging effect of the grid in characteristic distances $d_1$, $d_2$ and $d_3$ (Talbot effect). The relative position of the minima and maxima may in particular depend on the phase-shift of the wave front incident on beam splitter grating $G_1$. $d_1$ may in particular be in the order of several cm. If a monochromatic plane wave is incident on the beam-splitter grating that induces a phase shift of $\phi$, in particular by $\pi$, the intensity is split into two main diffraction orders, cancelling the zeroth order. The interference effects lead to an effect of self-imaging of the wave-front incident on $G_1$ at discrete distances downstream from $G_1$. This effect is referred to as the Talbot effect. E.g. at a distance $p1^2/8*lambda$, the phase modulation of the incident wave-front induced by $G_1$ is transformed into an intensity modulation with double frequency. The analyzer grating samples these modulations and allows to measure the phase-gradient induced by an object onto the x-ray wave-front via phase-stepping.

Figure 3A:
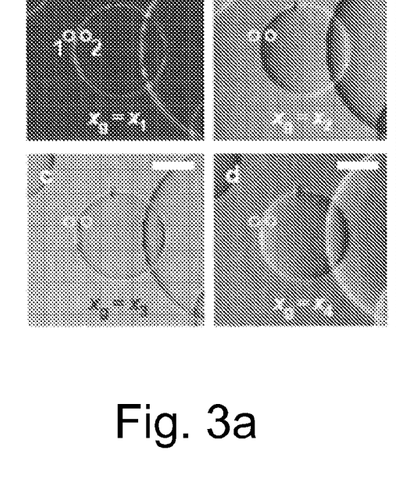
Figure 3B:
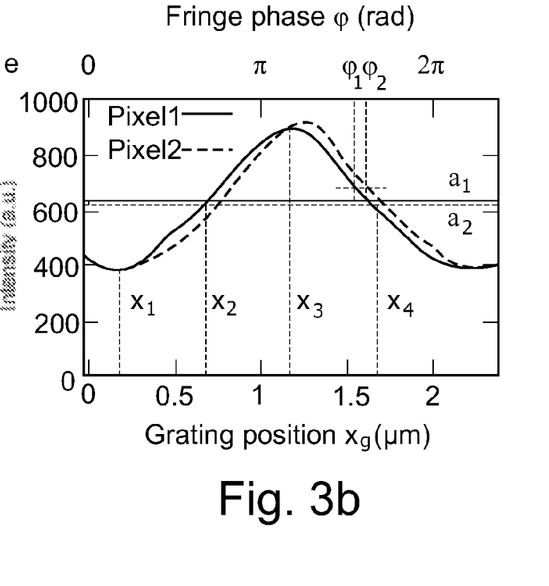

Now referring to FIGS. 3a,b, exemplary phase-contrast images acquired according to the present invention is depicted.

In FIG. 3a, exemplary four images are acquired of an object comprising individual bubbles by phase stepping employing four phase steps and thus four individual phase stepping states a-d. Distances $x_1$-$x_4$ relate to a displacement of grids $G_1$ versus $G_2$ for creating an intensity modulation. The full movement from $x_1$-$x_4$ is within one period of grating $G_2$ (<2 μm). The absorber grid or analyzer grid $G_2$ 10 is shifted in a direction x parallel to the grating planes. The difference in the wave front phase at two positions "1" and "2" may be extracted from the phase-shift $\phi_1$-$\phi_2$ of the measured intensity modulation, e.g. for four sampling positions $x_1$-$x_4$ in FIG. 3a.

Figure 4:
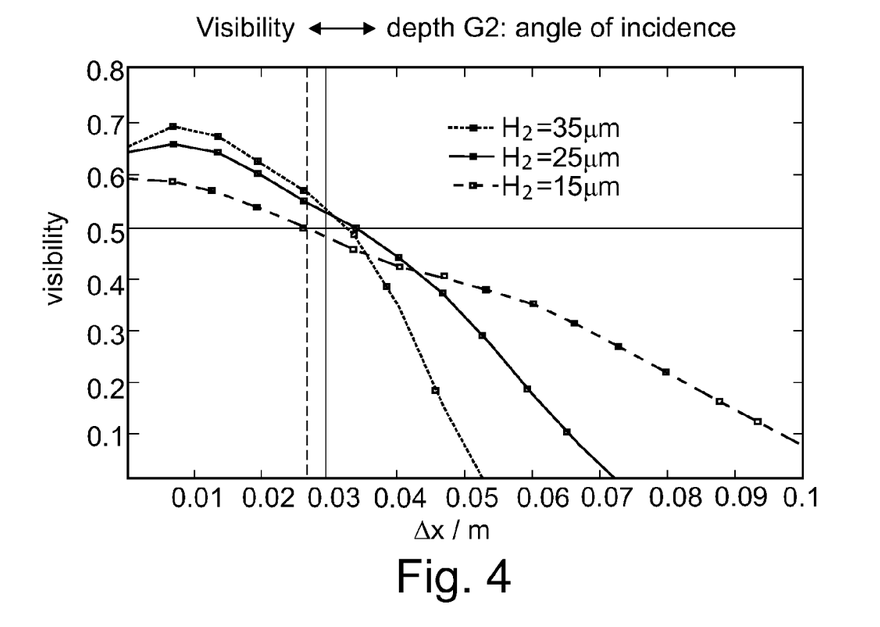
FIG. 4 shows exemplary visibility of interference fringes versus off axis position of a detector element pixel according to the present invention, FIG. 5a,b show an exemplary embodiment of a grating arrangement having an X-ray detector element according to the present invention.

Now referring to FIG. 4, exemplary visibility of interference fringes versus off axis position of a detector element pixel according to the present invention is depicted.

The degradation of the fringe visibility as a function of the off axis position of detector pixels may be taken from FIG. 4. A fringe visibility of 0.5 or greater may be considered to provide reasonable phase-contrast for image generation and processing. Three functions are provided in FIG. 4, depending on the height $H_2$ of the grating structure of grating $G_2$ (see FIG. 1c) providing deeper trenches in the grating, e.g. 35 μm, results in a diminished off axis visibility over a shallower grating depth $H_2$ of e.g. 15 μm. As may be taken from FIG. 4, a two-sided collimation has to be below 6 cm, thus Δx should be <3 cm, thereby limiting the usable size of planar detectors in phase-contrast imaging like e.g. differential phase-contrast mammography, to about 6 cm.

Figure 5A:
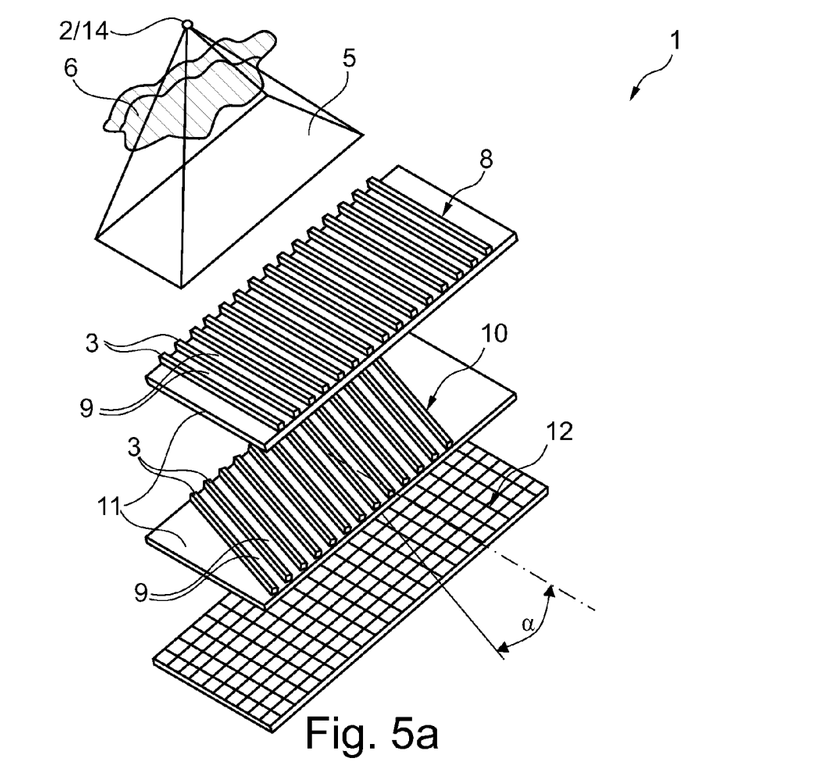
Figure 5B:
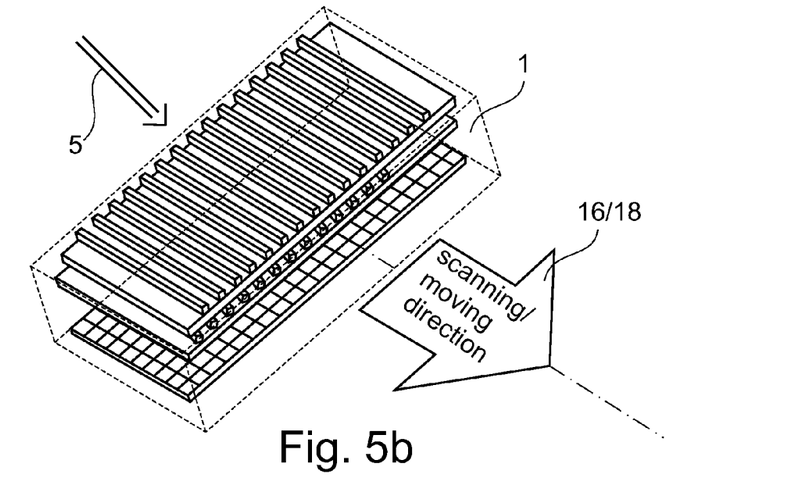

Now referring to FIGS. 5a,b, an exemplary embodiment of a grating arrangement having an X-ray detector element according to the present invention is depicted.

A first grating element, e.g. a beam splitter grating 8 and a second grating element, e.g. an analyzer grating 10 are arranged substantially parallel to one another and to an X-ray detector element 12. Each of the source grating 8 and the analyzer grating 10 comprises a base substrate 11, on which individual barrier regions 3 are arranged. Between barrier regions 3, trench regions 9 are arranged. The succession of barrier regions 3 and trench regions 9 constitute the trench structure or grating structure of the grating elements 8, 10.

In FIG. 5a, the trench structure of the analyzer grating 10 is exemplarily angled relative to the grating structure of the beam splitter grating 8 and the X-ray detector element array arrangement. However, it may also be conceivable that the trench structure of the analyzer grating 10 is parallel to the array structure of the X-ray detector element with the beam splitter grating 8 being tilted by angle α.

In FIG. 5a, X-radiation 5 is depicted exemplarily as a cone-beam emanating from X-ray source 2 having a focal spot 14. An object 6 is arranged in the cone-beam of X-radiation 5, which penetrates object 6 and subsequently arrives at the beam splitter grating 8, analyzer grating 10 and finally at X-ray detector element 12 for generating phase-contrast image information.

Now referring to FIG. 5b, the scanning movement of the grating arrangement 1 is depicted. Grating arrangement 1 is displaced in a scanning movement having a scanning or moving direction e.g. in a linear fashion. By the scanning movement, an image having a field of view larger than the size of X-ray detector 12 is obtainable, with an on the fly phase stepping due to the automatically rearranged grating arrangement relation of beam splitter grating 8 and analyzer grating 10, with respect to the X-ray source and the object to be examined 6.

Figure 6:
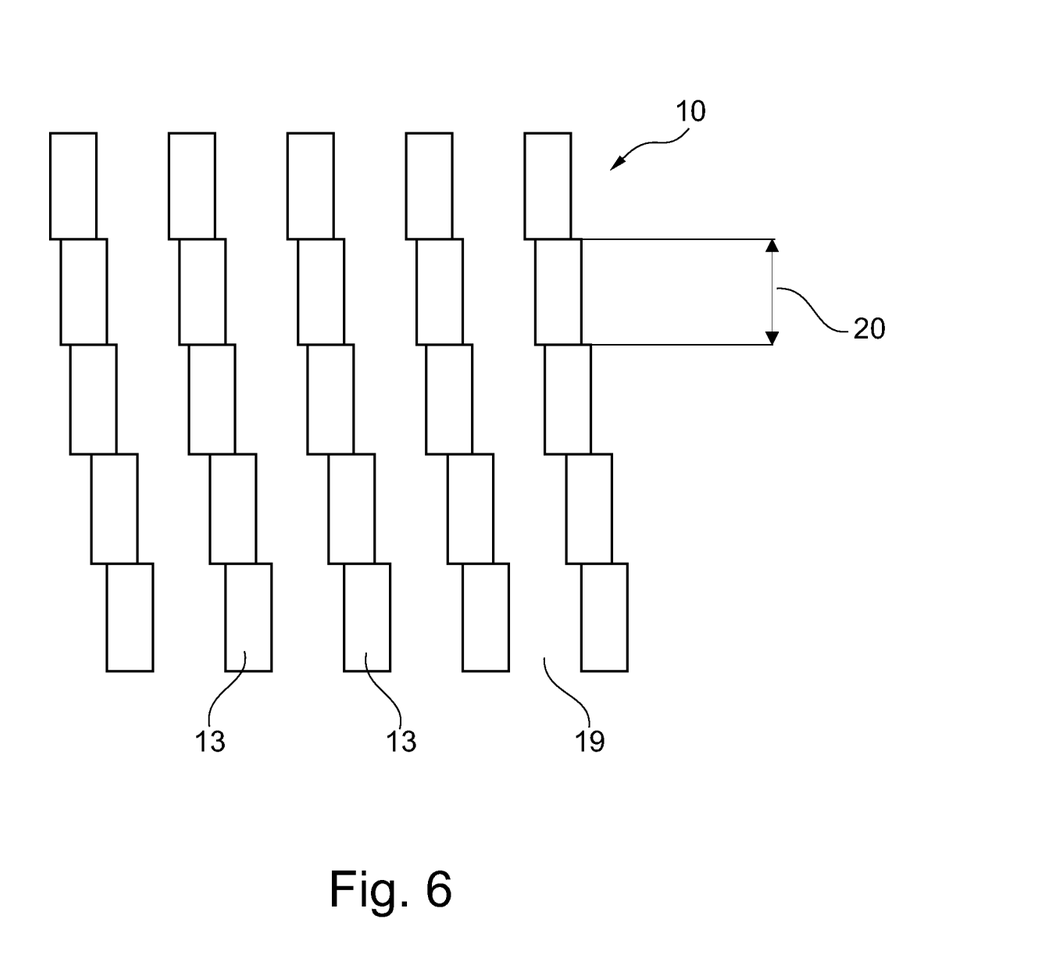
FIG. 6 shows a further exemplary embodiment of a grating element according to the present invention.

Now referring to FIG. 6, a further exemplary embodiment of a grating element according to the present invention is depicted.

The grating element according to FIG. 6 is exemplary an analyzer grating 10, in particular in accordance with features as described earlier, however may also be a phase shift grating. The grating structure of analyzer grating 10 of FIG. 6 comprises a sectionally discrete trench structure comprising barrier regions 13 and trench regions 19. The trench region may in particular be provided with a filling employing a high-z metal, e.g. gold (Au), not separately depicted in FIG. 6. The individual sectional barrier elements, constituting the barrier region 13, are arranged sectionally discrete having an elongation 20 of length. The elongation 20 may in particular be in the order of 1, 2, 3, 4, 5, 6, 7, 8 or more detector pixels.

The individual sectional barrier elements may each be considered to be aligned substantially parallel to the trench structure of a further grating element, e.g. a beam splitter grating 8, not depicted in FIG. 6. Each sectional barrier element is displaced to adjacent sectional barrier elements by an increment, thus, when employing a further grating element, may result in different phase stepping state. It may also conceivable, that the grating element of FIG. 6 not only comprises the discrete trench structure as depicted but is additionally angled with respect to a further grating element, as described above.

The lateral displacement of the sectional barrier elements of FIG. 6 may also comprise a sinusoidal or curved shape.

It should be noted that the term "comprising" does not exclude other elements or steps and that "a" or "an" does not exclude a plurality. Also, elements described in association with different embodiments may be combined.

It should also be noted, that reference numerals in the claims shall not be construed as limiting the scope of the claims.

LIST OF REFERENCE NUMERALS

1 Grating arrangement
2 X-ray source
3 Barrier region
4 Source grating $G_0$
5 X-radiation
6 Object
7 Optical axis
8 Beam splitter grating/phase grating $G_1$
9 Trench region
10 Analyzer grating/absorber grating $G_2$
11 Base substrate
12 X-ray detector element
13 Barrier region/sectional barrier elements
14 Focal spot
16 Linear movement
19 Trench region
20 Elongation of sectional barrier elements

The invention claimed is:

1. A grating arrangement for phase contrast imaging, comprising:
   a first grating element;
   a second grating element; and
   an X-ray detector element;
   wherein each of the first grating element and the second grating element comprises a trench structure;

wherein the trench structure comprises at least one trench region and at least one barrier region;

wherein the at least one trench region and at least one barrier region are at least locally arranged in parallel; and wherein the first grating element and the second grating element are arranged such that the trench structure of the first grating element and the trench structure of the second grating element are, at least locally, non-parallel, said arrangement being configured for displacing, in a scanning movement, the first and second grating elements, and said X-ray detector element, as a single unit.

2. The grating arrangement according to claim 1, wherein the first grating element and the second grating element are arranged substantially parallel.

3. The grating arrangement according to claim 1, wherein the first grating element is provided as a beam splitter grating; and/or wherein the second grating element is provided as an analyzer grating.

4. The grating arrangement according to claim 1, wherein the X-ray detector element is arranged substantially parallel to at least one of the first grating element and the second grating element.

5. The grating arrangement according to claim 1, wherein at least one of the first grating element and the second grating element is configured to influence at least one parameter of an amplitude and a phase of electromagnetic radiation.

6. The grating arrangement according to claim 1, wherein the trench structure of the first grating element and the trench structure of the second grating element comprise an angle α; and wherein α is in the range of 1° to 0.01°.

7. The grating arrangement according to claim 1, wherein the X-ray detector element comprises an array of X-ray detector element pixels; and wherein at least one of an X-ray detector element pixel, an X-ray detector element pixel row and an X-ray detector element pixel column corresponds to an individual phase stepping state achieved via stepping action in computer-controlled scanning.

8. An X-ray system, comprising an X-ray source; and a grating arrangement according to claim 1, wherein an object is arrangeable between the X-ray source and the grating arrangement; wherein the X-ray source and the grating arrangement are operatively coupled such that a phase contrast image of the object is obtainable.

9. The X-ray system according to claim 8, said X-ray detector element having a detector size; wherein the X-ray system is configured for acquiring a phase contrast image having a field of view larger than the detector size; wherein the grating arrangement is displaceable; and wherein by the displacement of the grating arrangement a phase contrast image having the field of view is obtainable.

10. The X-ray system according to claim 9, wherein the X-ray detector element is configured for acquiring a sub-region having the field of view.

11. The X-ray system according to claim 9, wherein at least one of the X-ray detector element and the grating arrangement is configured for scanning the field of view.

12. The X-ray system according to claim 8, wherein at least one of the X-ray detector element and the grating arrangement is displaceable, from at least one of a first position and an orientation, for acquiring first phase contrast image information to at least one of a second position, and an orientation, for acquiring second phase contrast information.

13. The X-ray system according to claim 8, further comprising a third grating element, serving as a source grating.

14. The X-ray system according to claim 13, wherein at least one of the X-ray source and the third grating element is displaceable relative to at least one of the first grating element, the second grating element, the object and the X-ray detector element.

15. A method for utilizing a grating arrangement according to claim 1 in at least one of an X-ray system, a CT-system, a mammography x-ray system, an inspection X-ray system, a security X-ray system, an industrial X-ray system and a tomosynthesis system, comprising:
providing said at least one of the systems; and
using said arrangement in one or more of said at least one of said systems.

16. The grating of claim 2, the first and second grating elements both having a grating pitch, said first and second gratings being displaced from mutual parallelism by less than said pitch.

17. The grating of claim 6, α being equal to one of: 0.1°, 0.2° and 0.3°.

18. The grating arrangement according to claim 1, said X-ray detector element having a flat surface for receiving X-rays, said surface being disposed substantially parallel to at least one of the first grating element and the second grating element.

19. The grating arrangement according to claim 1, the first and second grating elements being arranged one after another, in an X-ray beam receiving order.

20. The grating arrangement of claim 19, said single unit having defined spatial relationships of the three elements to one another.

21. The grating arrangement of claim 20 the first and second grating elements being physically in contact with said X-ray detector element.

* * * * *